United States Patent [19]

Mager et al.

[11] Patent Number: 5,679,755
[45] Date of Patent: Oct. 21, 1997

[54] CARBOSILANE DENDRIMERS, A METHOD OF PREPARING THEM AND THEIR USE

[75] Inventors: Michael Mager, Leverkusen; Aloys Eiling, Bochum; Martin Schloh, Köln, all of Germany

[73] Assignee: Bayer AG, Leverkusen, Germany

[21] Appl. No.: 641,848

[22] Filed: May 2, 1996

[30] Foreign Application Priority Data

May 16, 1995 [DE] Germany ............... 195 17 838.6

[51] Int. Cl.$^6$ ............................................. C08G 77/60
[52] U.S. Cl. ............... 528/35; 528/34; 556/479; 525/431; 525/464; 525/477
[58] Field of Search ............... 556/479; 528/35, 528/34; 525/431, 464, 477

[56] References Cited

U.S. PATENT DOCUMENTS 5,276,110  1/1994  Zhou et al. ............... 525/479

OTHER PUBLICATIONS van der Made et al., *Dendrimeric Silanes*, Advanced Materials, 1993, 5, No. 6, pp. 466–468.

Zhou et al., *Synthesis of Novel Carbosilane Dendritic Macromolecules*, Macromolecules, 1993, 26, pp. 963–968.

Seyferth et al., *Synthesis of an Organosilicon Dendrimer Containing 324 Si–H Bonds*, Organometallics, 1994, 13, pp. 2682–2690.

Mathias et al., *Hyperbranched Poly(siloxysilanes)*, Journal of the American Chemical Society, 1991, vol. 113, pp. 4043–4045.

Mathias et al., *Stars, Dendrimers and Hyperbranched Polymers: Towards Understanding Structure–Property Relationships for Single Molecule Constructs*, Polymer Preprints, Aug. 1993, 34, pp. 77–78.

Chang et al., *Synthesis and Characterizations of Oligocyclosiloxanes via the Hydrosilation of Vinylsilanes and Vinylsiloxanes with Heptamethylcyclotetrasiloxane*, Journal of Polymer Science: Part A, Polymer Chemistry, 1993, vol. 31, pp. 891–900.

Beatriz Alonso et al., *Organometallic Silicon Dendrimers*, J. Chem. Soc., Chem. Commun., 1994, pp. 2575–2576.

Primary Examiner—Melvyn I. Marquis
Attorney, Agent, or Firm—Connolly & Hutz

[57] ABSTRACT

The present invention relates to new carbosilane dendrimers, to a method of preparing them, and to their use.

13 Claims, No Drawings

CARBOSILANE DENDRIMERS, A METHOD OF PREPARING THEM AND THEIR USE

The present invention relates to new carbosilane dendrimers, to a method of preparing them and to their use.

The term dendrimers is used to describe strongly branched molecules with a highly ordered, mainly three-dimensional structure, the molecular weight of which falls within the range of that of oligomers or polymers.

Previously known carbosilane dendrimers were synthesised from an initiator nucleus by alternate hydrosilylation and Grignard reaction (see U.S. Pat. No. 5,276,110, Adv. Mater. 1993, 5, 466–468, Macromolecules 1993, 26, 963–968, J. Chem. Soc., Chem. Commun. 1994, 2575–2576 and Organometallics 1994, 13, 2682–2690, for example). The initiator molecule tetravinylsilane is for example reacted with $HSiCl_2CH_3$ in THF using a Pt catalyst. By reaction with vinylmagnesium halide a vinylsilane is again synthesised which is freshly available for hydrosilylation.

Dendrimers can be specifically synthesised with an exactly uniform molecular weight, whilst the usual polymers always display a certain molecular weight distribution.

This property predestines them for use as a reference substance in various analytical methods, such as for example electron microscopy and gel permeation chromatography. The incorporation of small particles in polymeric materials often results in an improvement in their property profile, particularly for example in their tensile strength, resistance to tear propagation or initial tearing resistance. The addition of pyrogenic hydrated silica to HTV or RTV silicone rubbers or synthetic rubber may be mentioned by way of example in this regard. Since the required reinforcement effect in polymers is greatest the smaller the particle size distribution, and transparency is retained with particle sizes significantly below the dimensions of visible light, carbosilane dendrimers are also suitable as fillers for polymers.

It has however often proved difficult to prepare high molecular weight carbosilane dendrimers which contain unreactive terminal groups and which have a uniform molecular weight (J. Am. Chem. Soc. 1991, 113, 4043–4044 and Polym. Prepr. 1993, 34, 77–78).

In the J. Polym. Sci., Part A, Polymer Chemistry (1993, 31, page 891 et seq., the synthesis of carbosilane dendrimers containing the unreactive terminal groups $—Si(OSiMe_3)_2Me$ is described. The separation of the reaction mixture obtained after synthesis was however only possible using gas-chromatographic methods.

The object of the present invention is therefore to provide high molecular weight, unreactive carbosilane dendrimers which have an exactly uniform particle size, can be prepared in pure form and are suitable both for incorporation in transparent plastics and for use as a calibration substance in analysis.

Surprisingly, it has now been found that carbosilane dendrimers containing terminal $OSiR^1R^2R^3$ radicals, where $R^1$, $R^2$, $R^3$, independently of each other, =alkyl or aryl radicals, fulfil these requirements.

The present invention therefore relates to carbosilane dendrimers of formula (I)

$$R_{4-i}Si[(CH_2)_nSiX_aR_{3-a}]_i \qquad (I)$$

where i=3 or 4, preferably i=4, and n=2–6, preferably n=2, where, when n appears more than once in a general formula for a molecule, n may have the same or different value within the general formula for the molecule and where the other radicals have the following meanings a) $X=OSiR^1R^2R^3$ where R, $R^1$, $R^2$, $R^3$, independently of each other, =alkyl or aryl radicals, and a=1 to 3, preferably a=3 with the exception of the combination n=2, $R=CH_3$ and a=2, or b) $X=[(CH_2)_nSiY_bR_{3-b}]y=OSiR^1R^2R^3$ where R, $R^1$, $R^2$, $R^3$, independently of each other, =alkyl or aryl radicals, and a, b, independently of each other, =1 to 3, preferably a=3 and b=3 or c) $X=[(CH_2)_nSiR_{3-a}[(CH_2)_nSiY_bR_{3-b}]_a]$ $Y=OSiR^1R^2R^3$ where R, $R^1$, $R^2$, $R^3$, independently of each other, =alkyl or aryl radicals, and a, b, independently of each other, =1 to 3, preferably a =3 and b =3 or d) $X=[(CH_2)_nSiR_{3-a}[(CH_2)_nSiR_{3-a}[(CH_2)_nSiY_bR_{3-b}]_a]_a]$ $Y=OSiR^1R^2R^3$ where R, $R^1$, $R^2$, $R^3$, independently of each other, =alkyl or aryl radicals, and a, b, independently of each other, =1 to 3, preferably a =3 and b =3.

The alkyl radicals R, $R^1$, $R^2$ or $R^3$ in the context of the invention are preferably linear or branched $C_1-C_5$ alkyl radicals which are optionally substituted. The aryl radicals R, $R^1$, $R^2$ or $R^3$ in the context of the invention are preferably $C_6$ rings which are optionally substituted.

In the context of the invention, the term "substituted" comprises all common substituents, such as halogen, alkyl, amine, etc.

Expressed as formulae, the carbosilane dendrimers according to the invention correspond to formulae (Ia–d)

$$R_{4-i}Si[(CH_2)_nSi(OSiR^1R^2R^3)_aR_{3-a}]_i \qquad (Ia)$$

or $$R_{4-i}Si[(CH_2)_nSiR_{3-a}[(CH_2)_nSi(OSiR^1R^2R^3)_bR_{3-b}]_a]_i \qquad (Ib)$$

or $$R_{4-i}Si[(CH_2)_nSiR_{3-a}[(CH_2)_nSiR_{3-a}[(CH_2)_nSi(OSiR^1R^2R^3)_bR_{3-b}]_a]_a]_i \qquad (Ic)$$

or $$R_{4-i}Si[(CH_2)_nSiR_{3-a}[(CH_2)_nSiR_{3-a}[(CH_2)_nSiR_{3-a}[(CH_2)_nSi(OSiR^1R^2R^3)_bR_{3-b}]_a]_a]_a]_i \qquad (Id).$$

In a preferred embodiment of the present invention the values of the indices n are the same within the molecule.

Carbosilane dendrimers of formulae $$Si[(CH_2)_2Si(OSiR^1R^2R^3)_3]_4$$

or $$Si[(CH_2)_2Si[(CH_2)_2Si(OSiR^1R^2R^3)_3]_3]_4$$

are particularly preferred.

The present invention also relates to a method of preparing carbosilane dendrimers of the formula Ia $$R_{4-i}Si[(CH_2)_nSiX_aR_{3-a}]_i \qquad (Ia)$$

where i=3 or 4 and n=2–6, where, when n appears more than once in a general formula for a molecule, n may have the same or different value within the general formula for the molecule and where the other radicals have the following meanings a) $X=OSiR^1R^2R^3$
  where R, $R^1$, $R^2$, $R^3$, independently of each other, =alkyl or aryl radicals, and
  a=1 to 3, or b) $X=[(CH_2)_nSiY_bR_{3-b}]_a]$ $Y=OSiR^1R^2R^3$
  where R, $R^1$, $R^2$, $R^3$, independently of each other, =alkyl or aryl radicals and
  a, b, independently of each other, =1 to 3, or c) $X=[(CH_2)_nSiR_{3-a}[(CH_2)_nSiY_bR_{3-b}]_a]Y=OSiR^1R^2R^3$
  where R, $R^1$, $R^2$, $R^3$, independently of each other, =alkyl or aryl radicals, and
  a, b, independently of each other, =1 to 3, or d) $X=[(CH_2)_nSiR_{3-a}[(CH_2)_nSiR_{3-a}[(CH_2)_nSiY_bR_{3-b}]_a]_a]$ $Y=OSiR^1R^2R^3$
  where R, $R^1$, $R^2$, $R^3$, independently of each other, =alkyl or aryl radicals, and
  a, b, independently of each other, =1 to 3, according to which method a dendrimer of formula (II)

(II)

with i=3 or 4, preferably i=4, and n=2–6, preferably n=2, and R=alkyl and/or aryl, where, when n appears more than once in a general formula for a molecule, n may have the same or different value within the general formula for the molecule and where the other radicals have the following meanings:

a) Z=Cl, Br, I, OR
  where c=1 to 3, or b) $Z=[(CH_2)_nSiW_dR_{3-d}]$
where c and d, independently of each other, =1 to 3, preferably c=3 and
  W hereinafter denotes Cl, Br, I or OR or c) $Z=[(CH_2)_nSiR_{3-c}[(CH_2)_nSiW_dR_{3-d}]_c]$
  where c and d, independently of each other, =1 to 3, preferably c=3, or d) $Z=[(CH_2)_nSiR_{3-c}[(CH_2)_nSiR_{3-c}[(CH_2)_nSiW_dR_{3-d}]_c]_c]$
  where c and d, independently of each other, =1 to 3, preferably c=3, is reacted with a triorganosilanolate, which is preferably used in excess, in a nonpolar solvent.

Expressed as formulae, compounds II a–d correspond to the formulae

 (IIa)

or

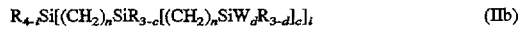 (IIb)

or

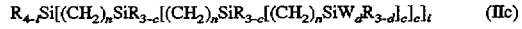 (IIc)

or

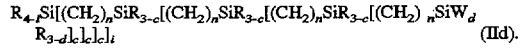 (IId).

Compounds of formula (IIa) are prepared by customary methods by the reaction of a suitable unsaturated silane with a hydridosilane, such as for example an alkoxy- or halogenosilane, in the presence of a catalyst, e.g. hexachloroplatinic acid in isopropanol, in a nonpolar solvent. The silanes of formula (IIa) which are obtained in this manner are reacted in a further step in a Grignard reaction with an alkenylmagnesium halide in aliphatic ether to form compounds having alkenylsilane functionality. The aforementioned steps are repeated for the preparation of compounds of formulae (IIb), (IIc) and (IId).

General preparation instructions for compounds IIa to IId are also given in U.S. Pat. No. 5,276,110, Adv. Mater. 1993, 5, 466–468, Macromolecules 1993, 26, 963–968, J. Chem. Soc., Chem. Commun. 1994, 2575–2576 and Organometallics 1994, 13, 2682–2690.

Triorganosilanolates in the context of the invention are preferably compounds of formula $MOSiR^1R^2R^3$, where M=Li, Na, K and $R^1$, $R^2$, $R^3$, independently of each other, =linear or branched, alkyl or aryl radicals, preferably optionally substituted $C_1$–$C_{10}$ alkyl and/or optionally substituted $C_6$ aryl radicals. In a preferred embodiment of the present invention, the radicals $R^1$ to $R^3$ uniformly represent methyl or ethyl groups. Sodium silanolates, and the use of carbosilane dendrimers containing $SiCl_cR_{3-c}$ terminal groups, are particularly preferred.

The preferred nonpolar solvents are aliphatic ethers. Diethyl ether is particularly preferred.

The method according to the invention is preferably carried out at temperatures ≧room temperature, more preferably at 25° to 50° C., most preferably at 30° C. The starting materials may be mixed in any sequence. However, the triorganosilanolate which is optionally present in excess is preferably initially introduced, with the subsequent addition of the carbosilane dendrimer.

In a preferred embodiment of the method according to the invention, a compound of formulae (IIa to d) is dissolved in a nonpolar solvent and is added drop-wise to a mixture comprising a triorganosilanolate in a nonpolar solvent, the total mixture being stirred for at least a further 20 hours.

The method according to the invention is preferably carried out with stirring.

The present invention also relates to the use of the carbosilane dendrimers according to the invention as a calibration substance in analytical methods, and as a filler in plastics, such as for example silicones, and in organic polymers such as polycarbonate, polyamide, polystyrene, etc.

The invention is explained in more detail by means of the following examples. The invention is however not restricted to these examples.

Practical examples

Preliminary remarks:

All the reactions were conducted by means of the Schlenk technique under argon or under vacuum. All the solvents used were dried by the usual laboratory methods before use and were used after distillation under argon. Purchasable starting materials were not subjected to further purification.

$^1$H NMR spectra were recorded at 400 or 500 MHz and proton-decoupled $^{13}$C spectra were recorded at 100 MHz using an AMX500 device manufactured by Bruker. A XR300 spectrometer manufactured by Varian was used at 60 MHz for recording proton-decoupled 29Si spectra. The mass spectra were prepared using Maldi measurements obtained using a Kratos Maldi 3 device manufactured by Shimatzu.

A 0.1% solution of hexachloroplatinic acid in absolute isopropanol was used as the hydrosilylation catalyst.

The compounds Si[(CH$_2$)$_2$SiCl$_3$]$_4$ and Si[(CH$_2$)$_2$Si[(CH$_2$)$_2$SiCl$_3$]$_3$]$_4$ can be prepared by the method described in Organometallics 1994, 13, 2682.

The compounds Si[(CH$_2$)$_2$Si[(CH$_2$)$_2$Si(CH$_3$)$_2$Cl]$_3$]$_4$ and Si[(CH$_2$)$_2$SiCl$_2$Me]$_4$ can be prepared analogously to the method described in Organometallics 1994, 13, 2682, using HSiCl(CH$_3$)$_2$ and HSiCl$_2$CH$_3$, respectively, as the silane component.

EXAMPLE 1

Synthesis of Si[(CH$_2$)$_2$Si(OSiMe$_3$)$_3$]$_4$ 10.8 g (15.9 mmole) Si[(CH$_2$)$_2$SiCl$_3$]$_4$ were dissolved in 10 ml diethyl ether and added drop-wise to 25 g (222.8 mole) sodium trimethylsilanolate in 60 ml diethyl ether. The reaction was strongly exothermic; drop-wise addition was effected sufficiently rapidly so that the diethyl ether boiled continuously. Thereafter the mixture was allowed to cool to room temperature, a further 40 ml diethyl ether were added and the mixture was stirred for a further 20 hours. Thereafter the mixture was diluted with 200 ml hexane, the organic phase was washed three times with 200 ml water each time and dried over MgSO$_4$, and the volatile constituents were removed under vacuum. A yellowish solid was obtained which was recrystallised from boiling acetone/methanol. The pure product precipitated as colourless crystalline needles.

The product was readily soluble in nonpolar solvents, such as for example pentane, hexane or methylene chloride.

Melting point: 68°–70° C.

| | Elemental analysis | | | |
|---|---|---|---|---|
| | C | H | O | Si |
| Calcd.: | 39.95% | 9.45% | 14.51% | 36.09% |
| Found: | 39.9% | 9.5% | 15.0% | 35.6% (Diff.) |

C$_{44}$H$_{124}$O$_{12}$Si$_{17}$ M=1322.917 g/mole
NMR: (CDCl$_3$)
$^1$H: δ=0.06 ppm (s, 27H, OSi(CH$_3$)$_3$); 0.28 ppm (m, 2H, SiCH$_2$); 0.46 ppm (m, 2H, SiCH$_2$).
$^{13}$C{$^1$H}: δ=1.37 ppm (s, OSi(CH$_3$)$_3$); 2.21 ppm (s, Si(CH$_2$)$_4$)$_i$; 6.08 ppm (s, OSiCH$_2$).
$^{29}$Si{$^1$H}: δ=−65.22 ppm (s, CH$_2$SiO); 6.87 ppm (s, OSiMe$_3$); 8.88 ppm (s, Si(CH$_2$)$_4$).
Mass spectrum: Calcd.: 1345.9 (M+Na) 1329.9 (M+Li) Found: 1345.8 1330.5

EXAMPLE 2

Synthesis of Si[(CH$_2$)$_2$Si[(CH$_2$)$_2$Si(OSiMe$_3$)$_3$]$_3$]$_4$ 12.6 g (5.71 mmole) Si[(CH$_2$)$_2$Si[(CH$_2$)$_2$SiCl$_3$]$_3$]$_4$ in 40 ml diethyl ether were added drop-wise with stirring to 25 g (222.8 mmole) sodium trimethylsilanolate in 130 ml diethyl ether. In the course of this procedure the reaction mixture was heated to boiling and the NaCl formed precipitated. After the addition was complete, the mixture was allowed to cool to room temperature and was stirred for 20 hours. 200 ml hexane was then added, the organic phase was washed four times with 200 ml water each time and dried over MgSO$_4$, and the volatile constituents were removed under vacuum. The oily residue was taken up in boiling acetone and the product was obtained on cooling as colourless, intergrown needles.

The product was readily soluble in nonpolar solvents, such as pentane, hexane or methylene chloride, for example.

| | Elemental analysis: | |
|---|---|---|
| | C | H |
| Calcd.: | 40.64% | 9.45% |
| Found: | 39.7% | 8.9% |

C$_{140}$H$_{388}$O$_{36}$Si$_{53}$ M=4137.137 g/mole
NMR: (CDCl$_3$)
$^1$H: δ=0.10 ppm (s, 81H, OSi(CH$_3$)$_3$); 0.38 ppm (m, 8H, SiCH$_2$); 0.53 ppm (m, 8H, SiCH$_2$).
$^{13}$C{$^1$H}: δ=2.11 ppm (s, OSi(CH$_3$)$_3$); 2.08 ppm, 2.69 ppm, 4.30 ppm und 6.80 ppm (s, SiCH$_2$).
$^{29}$Si{$^1$H}: δ=−64.96 ppm (s, CH$_2$SiO); 6.70 ppm (s, OSiMe$_3$); 7.90 ppm (s, Si(CH$_2$)$_4$), further Si—CH$_2$ signals not resolved.

EXAMPLE 3

Synthesis of Si[(CH$_2$)$_2$Si[(CH$_2$)$_2$Si(CH$_3$)$_2$OSiMe$_3$]$_3$]$_4$ 3.22 g (1.9 mmole) Si[(CH$_2$)$_2$Si[(CH$_2$)$_2$Si(CH$_3$)$_2$Cl]$_3$]$_4$ in 5 ml diethyl ether were added drop-wise to a solution of 2.96 g (26.4 mmole) sodium trimethylsilanolate in 20 ml diethyl ether. The drop-wise addition was effected sufficiently rapidly so that the solvent boiled gently. After the addition was complete, stirring was continued for a further 20 hours at room temperature, followed by dilution with 100 ml hexane. The organic phase was then washed three times with 60 ml water each time and dried over MgSO$_4$. After removing the volatile constituents under vacuum, the crude product was obtained as a yellow oil. It was taken up in 60 ml hexane and filtered through silica gel. The silica gel was washed twice with 20 ml hexane and the combined organic phases were freed from solvent under vacuum. The pale yellow oil was left under vacuum in a rotary evaporator for 20 hours and was thus freed from readily volatile constituents.

| | Elemental analysis: | | |
|---|---|---|---|
| | C | H | O |
| Calcd.: | 46.87% | 10.43% | 8.15% |
| Found: | 48.1% | 10.8% | 8.0% |

C$_{92}$H$_{244}$O$_{12}$Si$_{29}$ M=2357.419 g/mole
NMR: (CDCl$_3$):
$^1$H: δ=0.02 ppm (s, 18H, Si(CH$_3$)$_2$); 0.04 ppm (s, 27H, OSi(CH$_3$)$_3$); 0.34 ppm (m, 16H, SiCH$_2$).
$^{13}$C{$^1$H}: δ=−0.27 ppm (s, CH$_2$Si(CH$_3$)$_2$O); 2.06 ppm (s, OSi(CH$_3$)$_3$); 10.37 ppm (s, CH$_2$Si(CH$_3$)$_2$O); further SiCH$_2$ signals were masked or were too strongly broadened for interpretation.
$^{29}${Si}$^1$H): δ=6.25 ppm (s, OSiMe$_3$); 7.82 ppm und 7.87 (s, Si(CH$_2$)$_4$); 9.55 (s, CH$_2$Si(CH$_3$)$_2$O).

The product was readily miscible with nonpolar solvents, such as for example pentane, hexane or methylene chloride.

EXAMPLE 4

Preparation of Si[(CH$_2$)$_2$SiMe(OSiMe$_3$)$_2$]$_4$

A solution of 21.9 g (36.6 mmole) Si[(CH$_2$)$_2$SiCl$_2$Me]$_4$ in 40 ml diethyl ether was added drop-wise with stirring to 41.2 g (366.7 mmole) sodium trimethylsilanolate in 150 ml diethyl ether. Dropwise addition was effected sufficiently rapidly so that the solution boiled gently under reflux. After the addition was complete, the reaction mixture was stirred for a further 20 hours at room temperature and was then diluted with 200 ml hexane. After adding 200 ml water, the organic phase was separated, washed three times with 200 ml water each time and finally dried over magnesium sulfate. The ether and the hexane were then distilled off under vacuum in a rotary evaporator; the pale yellow oil which was thus obtained was then left under vacuum for a further 2 hours at 70° C. After cooling to room temperature, the oil was taken up in a small amount of hexane and filtered through silica gel. The latter was washed once with a little hexane and the combined organic phases were finally freed from solvent under vacuum. The pure oily product obtained tended to crystallise on the vessel wall.

The product was readily miscible with nonpolar solvents, such as for example pentane, hexane or methylene chloride.

NMR: (CDCl$_3$)

$^1$H: δ=0.02 ppm (s, 3H, SiC$\underline{H}_3$(OSi(CH$_3$)$_3$)$_2$); 0.10 ppm (s, 18H, SiCH$_3$(OSi(C$\underline{H}_3$)$_3$)$_2$); 0.31 ppm (m, 2H, SICH$_2$); 0.46 ppm (m, 2H, SiCH$_2$).

$^{13}$C{$^1$H}: δ=1.19 ppm (s, Si$\underline{C}$H$_3$(OSi(CH$_3$)$_3$)$_2$); 1.93 ppm (s, SiCH$_3$(OSi($\underline{C}$H$_3$)$_3$)$_2$); 2.23 ppm (s, Si(CH$_2$)$_4$); 9.69 ppm (s, $\underline{C}$H$_2$SiO).

What is claimed is:

1. Carbosilane dendrimers of general formula (I)

$$R_{4-i}Si[(CH_2)_nSiX_aR_{3-a}]_i \quad (I)$$

where i=3 or 4 and n=2–6, where, when n appears more than once in a general formula for a molecule, n may have the same or different value within the general formula for the molecule, and where the other radicals have the following meanings a) X=OSiR$^1$, R$^2$, R$^3$,
  where R, R$^1$, R$^2$, R$^3$, independently of each other, =alkyl or aryl radicals, and
  a=1 to 3, with the exception of compounds in which n=2, R=CH$_3$ and a=2, or b) X=[(CH$_2$)$_n$SiY$_b$R$_{3-b}$]Y=OSiR$^1$R$^2$R$^3$
  where R, R$^1$, R$^2$, R$^3$, independently of each other, =alkyl or aryl radicals, and
  a, b, independently of each other, =1 to 3, or c) X=[(CH$_2$)$_n$SiR$_{3-a}$[(CH$_2$)$_n$SiY$_b$R$_{3-b}$]$_a$]Y=OSiR$^1$R$^2$R$^3$
  where R, R$^1$, R$^2$, R$^3$, independently of each other, =alkyl or aryl radicals, and
  a, b, independently of each other, =1 to 3, or d) X=[(CH$_2$)$_n$SiR$_{3-a}$[(CH$_2$)$_n$SiR$_{3-a}$[(CH$_2$)$_n$SiY$_b$R$_{3-b}$]$_a$]$_a$]Y=OSiR$^1$R$^2$R$^3$
  where R, R$^1$, R$^2$, R$^3$, independently of each other, =alkyl or aryl radicals, and
  a, b, independently of each other, =1 to 3.

2. Carbosilane dendrimers according to claim 1, wherein n appears more than once in a general formula for a molecule and the values of n are equal within the general formula for the molecule.

3. Carbosilane dendrimers according to claim 1, characterised in that they are compounds of formula Si[(CH$_2$)$_2$Si(OSiR$^1$R$^2$R$^3$)$_3$]$_4$ or Si[(CH$_2$)$_2$Si[(CH$_2$)$_2$Si(OSiR$^1$R$^2$R$^3$)$_3$]$_3$]$_4$.

4. A method of preparing carbosilane dendrimers of the formula Ia $$R_{4-i}Si[(CH_2)_nSiX_aR_{3-a}]_i \quad (Ia)$$

where i=3 or 4 and n=2–6, where, when n appears more than once in a general formula for a molecule, n may have the same or different value within the general formula for the molecule and where the other radicals have the following meanings a) X=OSiR$^1$R$^2$R$^3$
  where R, R$^1$, R$^2$, R$^3$, independently of each other, =alkyl or aryl radicals, and
  a=1 or 3, or b) X=[(CH$_2$)$_n$SiY$_b$R$_{3-b}$]Y=OSiR$^1$R$^2$R$^3$
  where R, R$^1$, R$^2$, R$^3$, independently of each other, =alkyl or aryl radicals, and
  a, b, independently of each other, =1 to 3, or c) X=[(CH$_2$)$_n$SiR$_{3-a}$[(CH$_2$)$_n$SiY$_b$R$_{3-b}$]$_a$]Y=OSiR$^1$R$^2$R$^3$
  where R, R$^1$, R$^2$, R$^3$, independently of each other, =alkyl or aryl radicals, and
  a, b, independently of each other, =1 to 3, or d) X=[(CH$_2$)$_n$SiR$_{3-a}$[(CH$_2$)$_n$SiR$_{3-a}$[(CH$_2$)$_n$SiY$_b$R$_{3-b}$]$_a$]$_a$] Y=OSiR$^1$R$^2$R$^3$
  where R, R$^1$, R$^2$, R$^3$, independently of each other, =alkyl or aryl radicals, and
  a, b, independently of each other, =1 to 3, characterised in that a dendrimer of formula (II)

$$R_{4-i}Si[(CH_2)_nSiZ_cR_{3-c}]_i \quad (II)$$

where i=3 or 4, n=2–6 and R=alkyl and/or aryl, where, when n appears more than once in a general formula for a molecule, n may have the same or different value within the general formula for the molecule, and where the other radicals have the following meanings:

a) Z=Cl, Br, I, OR
  where c=1 to 3, or b) Z=[(CH$_2$)$_n$SiW$_d$R$_{3-d}$]
  where c and d, independently of each other, =1 to 3, and W hereinafter denotes Cl, Br, I or OR, or c) Z=[(CH$_2$)$_n$SiR$_{3-c}$[(CH$_2$)$_n$SiW$_d$R$_{3-d}$]$_c$]
  where c and d, independently of each other, =1 to 3, or d) Z=[(CH$_2$)$_n$SiR$_{3-c}$[(CH$_2$)$_n$SiR$_{3-c}$[(CH$_2$)$_n$SiW$_d$R$_{3-d}$]$_c$]$_c$]
  where c and d, independently of each other, =1 to 3, is reacted with a triorganosilanolate in a nonpolar solvent.

5. A method of preparing carbosilane dendrimers according to claim 4, characterised in that the triorganosilanolates have the formula MOSiR$^1$R$^2$R$^3$, where M=Li, Na, or K and R$^1$,R$^2$, R$^3$, independently of each other, =alkyl or aryl radicals.

6. A method according to claim 4, characterised in that sodium silanolates are used as the triorganosilanolates.

7. A method according to claim 4, characterised in that an aliphatic ether is used as the nonpolar solvents.

8. A method of using the carbosilane dendrimers of claim 1, wherein said method comprises the step of measuring the size of the carbosilane dendrimers to calibrate a device.

9. A method of using the carbosilane dendrimers according to claim 1, wherein said method comprises the step of incorporating the carbosilane dendrimers into a body of plastic as a filler material.

10. Carbosilane dendrimers according to claim 2, characterized in that they are compounds of formula $$Si[(CH_2)_2Si(OSiR^1R^2R^3)_3]_4$$

or $$Si[(CH_2)_2Si[(CH_2)_2Si(OSiR^1R^2R^3)_3]_3]_4.$$

11. A method according to claim 5, characterized in that sodium silanolates are used as the triorganosilanolates.

12. A method according to claim 5, characterized in that an aliphatic ether is used as the nonpolar solvent.

13. A method according to claim 6, characterized in that an aliphatic ether is used as the nonpolar solvent.

* * * * *